US009218735B2

(12) United States Patent
Gegner et al.

(10) Patent No.: US 9,218,735 B2
(45) Date of Patent: Dec. 22, 2015

(54) WIRELESS PATIENT MONITORING SYSTEM AND METHOD FOR MONITORING THE PHYSIOLOGICAL STATUS OF A PATIENT HAVING A NETWORK ACCESS POINT

(75) Inventors: Guenter Gegner, Tuebingen (DE); Harald Greiner, Nufringen (DE); Martin Bufe, Ebersbach (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 256 days.

(21) Appl. No.: 13/977,922

(22) PCT Filed: Dec. 27, 2011

(86) PCT No.: PCT/IB2011/055961
§ 371 (c)(1),
(2), (4) Date: Jul. 2, 2013

(87) PCT Pub. No.: WO2012/093319
PCT Pub. Date: Jul. 12, 2012

(65) Prior Publication Data
US 2013/0293373 A1    Nov. 7, 2013

(30) Foreign Application Priority Data
Jan. 6, 2011    (EP) .................................... 11150328

(51) Int. Cl.
G08B 21/00    (2006.01)
G08B 25/00    (2006.01)
A61B 5/00    (2006.01)
G06F 19/00    (2011.01)

(52) U.S. Cl.
CPC .............. *G08B 25/00* (2013.01); *A61B 5/0002* (2013.01); *G06F 19/3418* (2013.01); *A61B 5/68* (2013.01)

(58) Field of Classification Search
CPC ....................................................... G08B 25/00
USPC ........ 340/527, 539.1, 539.12, 573.1; 600/300
See application file for complete search history.

(56) References Cited

U.S. PATENT DOCUMENTS

| 7,098,803 B2 | 8/2006 | Mann et al. |
| 8,622,902 B2 | 1/2014 | Woehrle |
| 2004/0236189 A1 | 11/2004 | Hawthorne et al. |
| 2007/0251835 A1 | 11/2007 | Mehta et al. |
| 2007/0253021 A1 | 11/2007 | Mehta et al. |

FOREIGN PATENT DOCUMENTS

| CN | 101422366 A | 5/2009 |
| CN | 101430817 A | 5/2009 |
| EP | 1422677 A2 | 5/2004 |
| WO | 9913765 A1 | 3/1999 |

*Primary Examiner* — Jeffery Hofsass

(57) ABSTRACT

The invention relates to a patient monitoring system comprising at least one monitoring unit (24) for monitoring the physiological status of a patient and a host system (14) comprising a network of access points (16, 18, 20) for wireless reception of physiological status data. Each monitoring unit (24) is provided to transmit physiological status data to the access points at selected points of time, together with time related data indicating the expected point of time of the next data transmission. The invention further relates to a respective method for monitoring the physiological status of a patient.

10 Claims, 3 Drawing Sheets

WIRELESS PATIENT MONITORING SYSTEM AND METHOD FOR MONITORING THE PHYSIOLOGICAL STATUS OF A PATIENT HAVING A NETWORK ACCESS POINT

FIELD OF THE INVENTION

The invention relates to the field of patient monitoring by means of monitoring units that are wirelessly connected to a host system comprising a network of access points for wireless reception of data acquired by the monitoring units.

BACKGROUND OF THE INVENTION

In a hospital setting it is desired to monitor a number of different patients at the same time by means of one monitoring system that acquires data related to the vital signs, i.e. the physiological status of the patients and provides the nursing staff with respective notifications about their status. For a setting with non-critical patients who are able to move freely within the hospital, wireless systems have been developed that comprise monitoring units that can be worn by the patients. These monitoring units comprise sensors for monitoring the vital signs and means for transmitting corresponding physiological data to a host system. To cover the area completely in which the patients are located, different access points (so-called hotspots) are arranged so that a patient wearing a monitoring unit is always in reach of one of these access points to provide a wireless communication with the host system.

In an ideal situation each monitoring unit of the patient monitoring system is always in reach of an access point so that a communication between the monitoring units and the host system is established at any desired point of time. However, in practice such a complete monitoring cannot be guaranteed. It may happen that the patient wearing a monitoring unit enters a zone that is not covered by the reception area of any access point, so that the communication between the monitoring unit and the host system is interrupted. This is the reason why the time of the measurement of physiological status data and the time of transmission of these data are decoupled. When the host system determines that no data transmission has occurred according to the predetermined time schedule, an alarm is activated to notify the nursing staff that no physiological data related to the respective patient are present in the system and that no monitoring of this patient takes place. However, this may result in situations in which the nursing staff is alarmed only because of an interruption of the connection although there is no critical status of the patient to be cared for.

US 2004/0236189 A1 discloses a patient monitoring system comprising a wireless network with monitoring units that communicate with a modem as a central monitoring station. When the monitoring units fail to communicate on time schedule, the modem generates an alert. However, the generation of this alert is based on a fixed time schedule, leading to the same problems as described above, namely to the generation of many faults alarms due to a non-critical temporary interruption of the connection between the monitoring unit and the network.

SUMMARY OF THE INVENTION

It is an object of the invention to provide a patient monitoring system as mentioned above that relieves the workload of the caregiving personal by an improved management of data transmission between the monitoring units and the host system with respect to the time schedule of data transmission, avoiding the generation of alarms in non-critical situations. Another object is the provision of a corresponding method for monitoring the physiological status of a patient.

These objects are achieved by a patient monitoring system as well as by a method as claimed in the independent claims.

In the patient monitoring system according to the present invention, the at least one monitoring unit may transmit data related to the physiological status of the patient at selected points of time together with data that contain an information about the next point of time when a transmission is to be expected. This time related information can be interpreted by the host system so as not to expect the next data transmission earlier than it is communicated by the respective monitoring unit, and an unnecessary alarm is avoided. This is an advantage over fixed time schedules in which the transmission of measured data is expected in predetermined time intervals. Moreover, when the expected point of time of a data transmission has expired, it is possible to wait some time before generating alarm. For example, when the announced time for data transmission is expired, a notification can be generated that is output to a user. However, an alarm may only be generated after an additional time period has passed and a data transmission has not occurred in the meantime. It results from the above that the patient monitoring system according to the present invention can handle the time schedule for the transmission of data to the host system in a more flexible way, avoiding a lot of unnecessary critical alarm situations and providing an intelligent management of the transmission and interpretation of data. The data related to the physiological status of a patient may be represented by temperature, blood pressure or heart rate. However, also signals relating to the blood pressure cuff may be transmitted. Thus, in case of a removed cuff, the removed status may be signaled. Together with the data related to the physiological status, the name and/or the location of the patient may be transmitted and displayed.

According to one preferred embodiment of the present invention, the host system is provided to determine whether an expected point of time of a data transmission has expired without receiving further physiological status data from the respective monitoring unit and to output a notification according to the result of this determination. When this result is positive, i.e. no physiological status data has been received from the respective monitoring unit at the announced point of time, the nursing staff may be notified accordingly in form of a status indication. Such a notification may not be necessarily be an alarm that requires an immediate reaction. A notification may be just the visual displaying of the status of a respective monitoring unit, without any audible signal.

According to another preferred embodiment, the host system is provided to output an alarm signal delayed after the expiration of an expected point of time of a data transmission without a reception of further physiological status data from the respective monitoring unit. This means that after the expected point of time is expired, the host system waits for a certain delay time period that can be predetermined. During that time period, a notification can be output, as described above. However, after the expiry of this additional time period, an alarm signal is output to inform the nursing staff that a critical situation may have occurred. For example, the alarm can be output together with the information that there was no data transmission for a time period measured since the last transmission. A time threshold can be provided to generate the alarm when the threshold is exceeded.

Preferably the delay time is one of the following: a fixed delay time; a delay time depending on at least one measurement interval of at least one physiological parameter of the patient; or a delay time depending on the present physiological status of the patient. For example, the delay time before generating the alarm can be shortened in case it is determined that the status of the patient shows a tendency to deteriorate. Another possibility is to adapt the delay time to a measurement period or interval of a physiological parameter. This can also be one of a plurality of different measurement periods for different parameters (for example, the shortest or the longest of these intervals). Moreover, the delay time can be calculated on the basis of one or more of such measurement periods.

According to another preferred embodiment, the host system is provided to output alarm signals having a predetermined characteristic, like an intensity increasing with the time expired after an expected point of time of a data transmission without a reception of further physiological status data from the respective monitoring unit. For example, a first alarm signal having a low intensity can be generated at a point of time delayed after the expiration of the expected point of time of the data transmission. After a further additional time delay, a second alarm signal having a higher intensity than the first alarm signal is generated, and so on. The intensity may be audible signal and/or the kind of visual displaying the status. Thus, color and size of monitoring unit on a display maybe changed from a notification to a first alarm and a second alarm. Thus, for a notification the color of a monitoring unit may be normal, e.g. blue, wherein in case of a first alarm the color may change into red, wherein for indicating the second alarm also the size of the red indication of the respective monitoring may change to large symbol. This allows the generation of alarm signals of increasing intensity, indicating an increasing urgency of the status situation. The different intensities of alarm signals may correspond to different time thresholds, i.e. subsequent delay times that are determined on a suitable basis. That is, the delay times may be fixed or determined on the basis of the present physiological status of the patient or depending on measurement intervals of the physiological parameters, as described above.

In one possible embodiment the monitoring units are provided for transmitting physiological status data together with the time related data immediately or directly after measurement of these physiological status data. In this case the physiological status data are transmitted as one data package at one (expected) point of time to an access point. Due to the limited battery lifespan of a monitoring unit it may be preferred to active the monitoring unit periodically. Here it may be advantageously to measure the physiological data and send the acquired data during the same activation phase to efficiently use the power of the battery.

Preferably the expected point of time of a next data transmission is determined by the respective monitoring unit. In this case each monitoring unit manages its own time schedule concerning the transmission of data to the host system via the access points.

According to another embodiment of the present invention, each access point is provided to transmit data to the monitoring units, and the host system is provided to determine and to communicate the expected points of time of the next data transmissions to the respective monitoring units. In this case the management of the time schedule is provided by the host system, and the points of time when data shall be transmitted back to the host system are communicated to the monitoring units.

Preferably each of the monitoring units is provided to transmit data indicating the remaining battery lifetime of this monitoring unit together with the physiological status data and time related data. The battery lifetime is an important information concerning the status of the monitoring unit, and when the remaining battery lifetime is short, the host system may output an alarm signal so that a user can react to this situation.

According to another preferred embodiment, the host system is provided to submit status information to a monitoring system. Such an external monitoring system may be a hospital system that manages different patient monitoring systems. For example, a critical status indication to which the caregiving personal has not reacted may be communicated to the external monitoring system to provide an additional supervision function.

According to another preferred embodiment of the present invention, the host system comprises a display for displaying status information of the monitoring units. For example, the display may be a screen that displays the status of different monitoring units at the same time, ordered according to the urgency of intervention so that it represents a worklist for the caregiving personal. Another possibility is to order the different monitoring units according to the location, i.e. the access points to which they are connected wirelessly. The possibility may be provided to choose between different kinds of displaying depending on the situation to be checked by the nursing staff Thus, the display may periodically display the battery information of the monitoring units to signal early enough and maybe to avoid a breakdown of the battery of a monitoring unit resulting in a lack of transmission capability.

According to the present invention, a method for monitoring the physiological status of a patient comprises measuring the physiological status data of a patient by means of a monitoring unit, and transmitting the measured physiological status data to an access point, together with time related data containing information about an expected point of time of the next data transmission of this monitoring unit.

According to a preferred embodiment of this method, it comprises the determination whether an expected point of time of the data transmission has expired without receiving further physiological status data from the respective monitoring unit, and the output of a corresponding notification according to the result of this determination.

Another preferred embodiment of this method comprises the output of an alarm signal delayed after the expiration of an expected point of time of a data transmission without further reception of further physiological status data from the respective monitoring unit.

According to another preferred embodiment, this method further comprises the output of alarm signals of an intensity increasing with the time expired since an expected point of time of a data transmission without a reception of further physiological status data from the respective monitoring unit.

BRIEF DESCRIPTION OF THE DRAWINGS

These and other aspects of the invention will be apparent from and elucidated with reference to the embodiments described hereinafter. In the drawings.

DETAILED DESCRIPTION OF EMBODIMENTS

Figure 1:
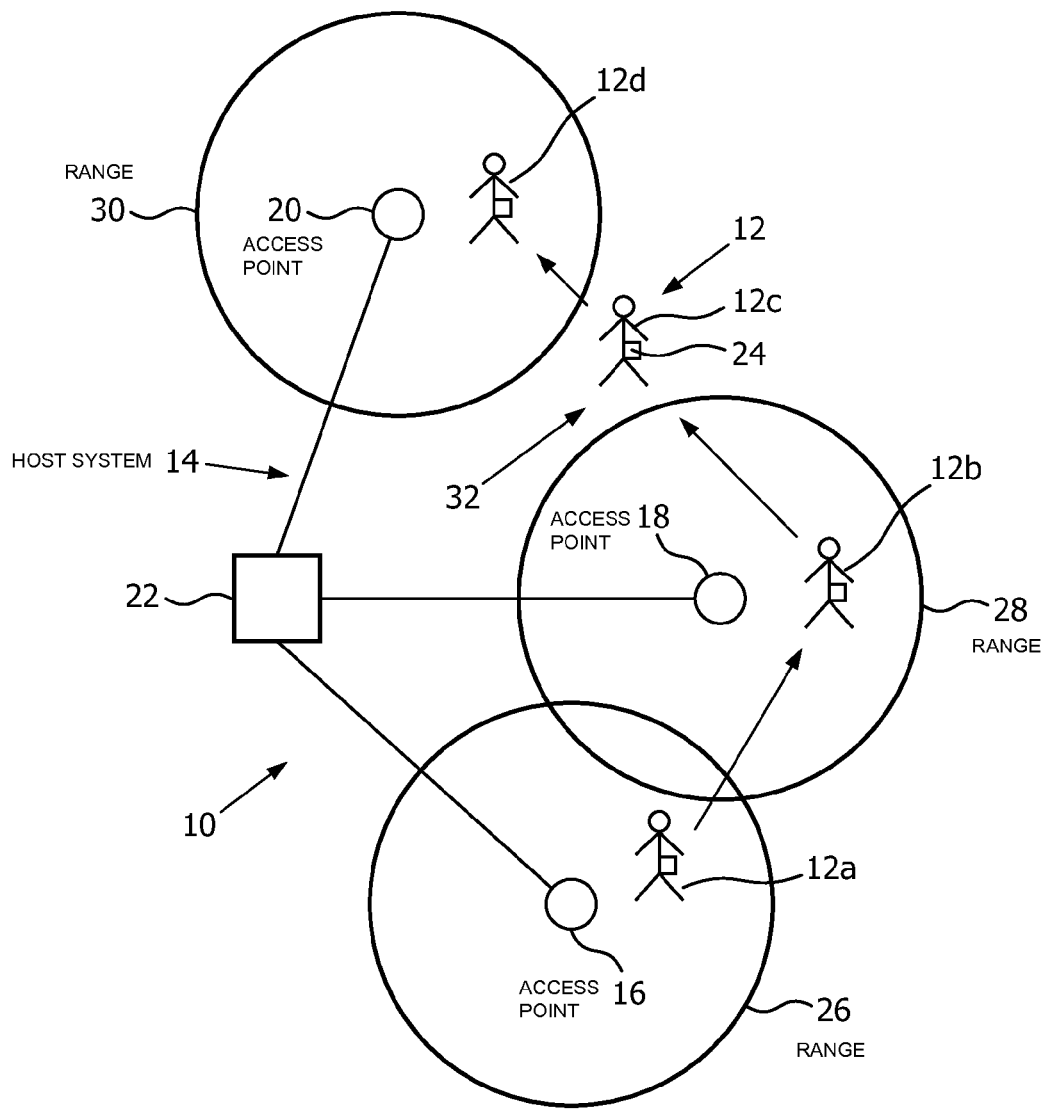
FIG. 1 is a schematic view of one embodiment of a patient monitoring system according to the present invention.

The patient monitoring system 10 in FIG. 1 is installed in a hospital environment to monitor patients that are able to move around in the hospital area. As one example, one patient 12 is shown in four different positions denoted by 12a, 12b, 12c and 12d. In the following it will be assumed that the patient 12 moves from the first position 12a to 12b as the second position, further to 12c as a third position and to 12d as the final position.

The patient monitoring system comprises a host system 14 with a network of access points 16, 18, 20 that are provided for wireless reception of data and to further transmit these data wirelessly or wired to a central processing unit 22 of the host system 14.

Moreover, the patient monitoring system 10 comprises portable monitoring units 24 that are carried around by the patients 12. Each patient 12 wears one monitoring unit 24.

The monitoring unit 24 is provided with sensors for monitoring the physiological status of a patient, e.g. to obtain information related to her/his vital signs. Moreover, the monitoring units comprise transmitters for transmitting the physiological status data that have been acquired by the sensors of this monitoring unit 24 wirelessly to the access points 16, 18, 20. The physiological status data transmitted by the monitoring units 24 are forwarded by the access points 16, 18, 20 to the central processing unit 22 for further analysis of the vital signs of the patient 12.

Each access point 16, 18, 20 has a limited range for receiving data from the monitoring units 24. In FIG. 1, the ranges of the access points 16, 18, 20 are denoted by circles 26, 28, 30 around the respective access points 16, 18, 20. The ranges may overlap, as shown with the ranges 26 and 28 of the access points 16 and 18. However, the ranges 28 and 30 of the access points 18 and 20 may also not overlap. Consequently there is a zone 32 between the ranges 28 and 30 in which no communication is possible between the monitoring unit 24 and the access points 16, 18, 20.

The monitoring units 24 transmit physiological status data to the access points 16, 18, 20 of the network only at selected points of time. The acquisition of the physiological status data can take place in the time intervals between the data transmissions, wherein the physiological status data are stored within the monitoring units 24 and transmitted as data packages to the access points 16, 18, 20 at selected time points. However, it is also possible to carry out the measurements of the physiological status data immediately before (or at) the time points of transmission so that the data acquisition and data transmission to the access points 16, 18, 20 take place almost at the same time to further increase the energy efficiency of a monitoring unit, which may be switched in an inactive mode or a power saving mode after transmitting its data packet until the next transmission of data has been scheduled.

In the present embodiments, the time intervals between the points of time of data transmission may be determined individually by the respective monitoring unit 24. Each time a data transmission from a monitoring unit 24 to an access point 16, 18, 20 is performed, the monitoring unit 24 transmits not only physiological status data to the access point 16, 18, 20 but also time related data containing an information about the point of time when the next data transmission is to be expected. With other words, with each data transmission from the monitoring unit 24 to an access point 16, 18, 20, the host system 14 acquires an information about the time of the next data transmission.

Thus, there is no fixed time schedule for data transmissions from the monitoring units 24 to the access points 16, 18, 20 with predetermined time intervals lying between the points of time of the subsequent data transmissions, but the time schedule is flexible and can be adapted to the layout of the network of access points 16, 18, 20 with respect to their accessibility, i.e. the arrangement of the ranges 26, 28, 30 and the possibilities of a patient 12 to move between different ranges 26, 28, 30 and to change from one range to the other. For example, the patient 12 may move from a starting position 12a to the second position 12b to change between ranges 26 and 28 of two access points 16 and 18 that are close to another having overlapping ranges 26, 28. In such situation no interruption of accessibility is to be expected, and data transmissions from the monitoring unit 24 to one of the access points 16, 18 will be possible always from position 12a to position 12b (indicated by an arrow). Consequently the expected point of time for respective the next data transmission may lie in the near future so that a transmission of measurement results can take place in very short time intervals, if desired.

However, on the way from position 12b to position 12d over position 12c, the situation is different. In this case the patient 12 crosses a zone 32 (indicated by the intermediate position 12c) in which no communication between the monitoring unit 24 and the access points 18 or 20 is possible. This interruption of connection may be precalculated when a data transmission takes place in position 12b, and the time related data sent in this position 12b indicate that the next data transmission will take place in the further future, i.e. after a longer time interval when the patient has reached range 30 of the next access point 20. The precalculation of a next data transmission may be based on knowledge of the reception areas of the access points and/or based on directions of movements of a patient. Furthermore, the monitoring unit may notice a decreased signal from the access point and may decide by its own to send its current physiological data together with information for an extended delay, when a next data transmission could be expected by the host system. Transmissions of data are avoided when the patient 12 moves within the zone 32, and the next transmission is postponed to a point in time when another range of access point has been reached.

On the basis of the information received within each data transmission from the monitoring units 24, the host system 14 is enabled to determine whether an expected point of time of a data transmission (as announced with the last data transmission) has expired without reception of further physiological status data from the respective monitoring unit 24. In this case a notification can be output that informs a user, for example, the nursing staff personal about this expiration without any reception of physiological status data. This notification can be displayed, for example, on a screen. For example, the user can be notified that there is no data reception from the specified monitoring unit for a certain time interval (which may also be specified within this notification). This notification does not necessarily have an alarming character because it is merely an information that the patient 12 wearing this monitoring unit 24 is out of range of the host system 14. However, an alarm signal may be generated by the host system 14 at a later point of time delayed after the expiration of an expected point of time of a data transmission when no further physiological status data have been received from the respective monitoring unit 24. This means that the host system 14 will wait for some time after the expiration of the point of time of the next data transmission. When a data transmission takes place within this delayed time after the expiration from the same monitoring unit 24, the alarm will be dispensed.

It is possible to generate the alarm after a fixed delay time after the expiration of the expected point of time of a data transmission. For example, the alarm could be generated when no physiological status data have been received since X minutes, where the number X is a fixed time delay. However, in a preferred embodiment this time delay is a variable depending on the present status of the patient that is calculated by the host system 14 on the basis of present physiological status data. For example, the time delay can be shortened in case the physiological status of the patient has a tendency to deteriorate. Alternatively the time delay depends on time intervals for measuring the physiological status data. For example, when a selected physiological parameter is to be measured within determined measurement periods, the delay time will be chosen according to this measurement period. With other words, when no data concerning this physiological parameter are received at an expected point of time, the host system 14 will wait another measurement period to receive these data before generating the alarm. It is, however, possible to calculate the delay time for the alarm in a different way based on the measurement periods. For example, if the physiological status data comprise different physiological parameters to be measured within different measurement periods, the delay time for generating the alarm may be based on the shortest of these measurement periods, on the longest of these measurement periods, or be calculated depending on more than one measurement period.

The host system 14 may further provide an escalation mechanism by outputting alarm signals of increasing intensity, wherein the intensity increases with the time expired after an expected point of time of a data transmission from a selected monitoring unit 24 without a reception of further physiological status data. Predetermined time thresholds could be provided and after a further time threshold is exceeded, an additional alarm of increased intensity is generated. It is possible to calculate these thresholds on the basis of measurement periods of one or more physiological parameters, as described above. For example, each further threshold may correspond to the expiry of another measurement period of a physiological parameter. Exceeding a certain time threshold may provide the respected monitoring unit 24 with a certain alarm status, which can be displayed on a display device to the user. In this display, the monitoring units 24 may be ordered according to their alarm status, beginning with the highest alarm level. This provides the user with an additional information about the priority of the different alarm status of the monitoring units 24. It is, of course, possible to display any other status information of the monitoring units to the user.

One example for such an additional status information is the remaining battery lifetime of a monitoring unit 24. Data indicating the remaining battery lifetime can be transmitted together with the physiological status data and the time related data referring to the expected point of time of the next data transmission. The information about the remaining battery lifetime may be acknowledged when an alarm status is provided to the monitoring unit 24. A low battery lifetime may indicate a higher alarm status, since it requires an intervention by the caregiving personal.

The host system 14 shown in FIG. 1 can be connected to an external monitoring system that is not shown in the figures. Such an external monitoring system can be a hospital system that supervises the shown host system 14. Any status information or other information received by the monitoring units 24 can be transmitted by the host system 14 to the external monitoring system. For example, a high priority alarm status of a monitoring unit 24 that exists already for a longer time period without any intervention by the caregiving personal can be transmitted to the external monitoring system so that an additional safety mechanism is established.

In the above example the access points 16, 18, 20 are only provided to receive data from the monitoring units 24. However, it is also possible to provide the access points 16, 18, 20 as transceivers to combine a transmitting and a receiving function. In this case each access point 16, 18, 20 is also provided to transmit data to the monitoring units 24, for example, control data. In this setting the host system 14 may also be provided to determine the expected points of time of the next data transmissions and to communicate them to the respective monitoring units 24. This means that the calculation of the expected points of time of the next data transmissions is performed by the central processing unit 22 of the host system 14.

It is further possible to transmit an alarm output by the host system to the nursing staff also to the respective monitoring unit causing the alarm to urge the patient to move to a nursing staff to personally introduce himself for verifying the non-critical situation. This function may provide flexibility also to patient, which are normally not allowed to leave a certain area without any supervision.

It is noted that in the above example, any calculation operations of the host system 14 are performed by its central processing unit 22, and the connections between the central processing unit 22 and the access points 16, 18, 20 may be provided at least for the transmission of data from the access points 16, 18, 20 to the central processing unit 22 or be provided for bidirectional communication, i.e. also for transmitting data from the central processing unit 22 to the access points 16, 18, 20. This connection may not necessarily be established wirelessly but can also be based on wired connections.

Figure 2:
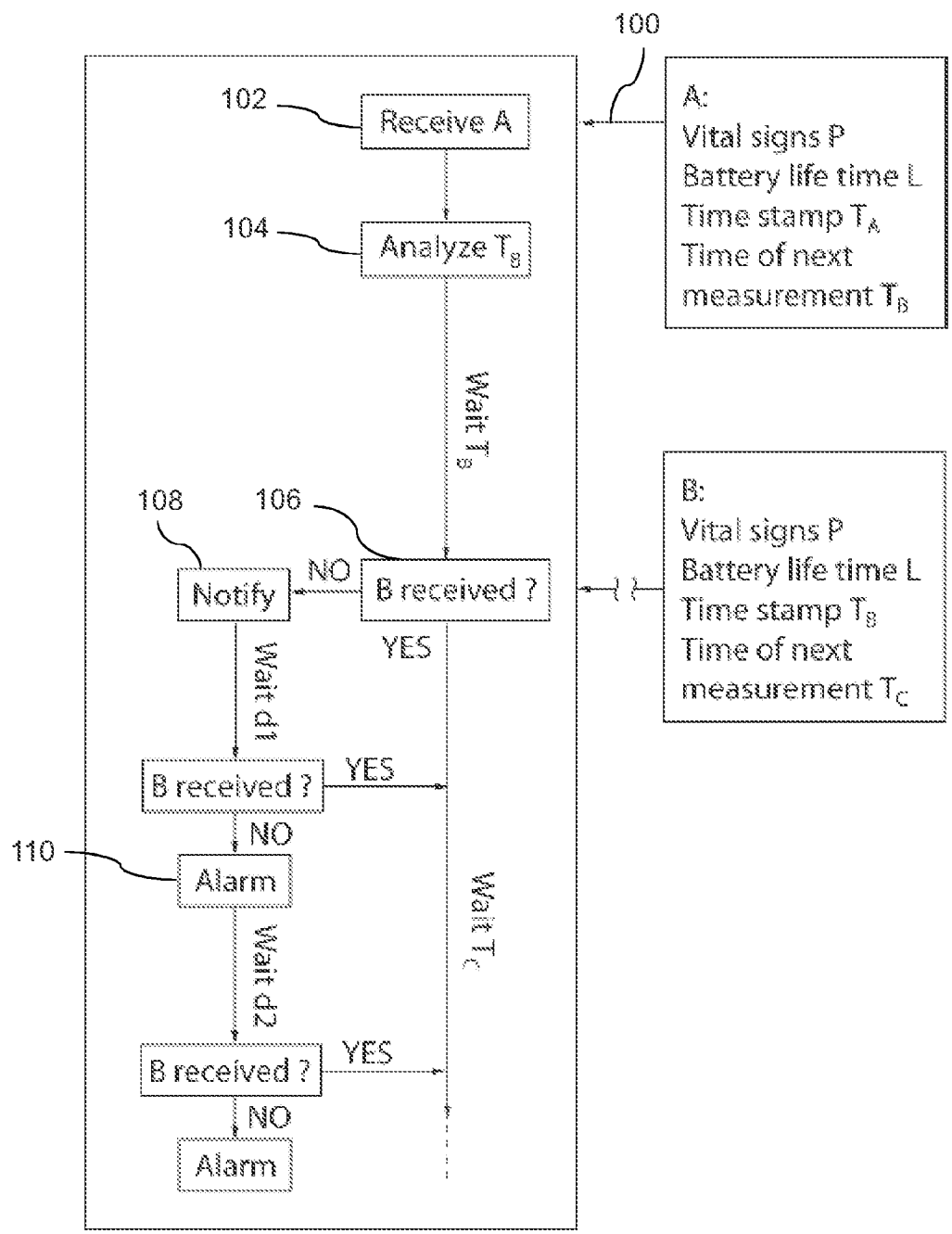
FIG. 2 is a diagram showing the communication between at least one monitoring unit and the host system of the patient monitoring system shown in FIG. 1.

FIG. 2 is a diagram showing the activities of one monitoring unit 24 of the patient monitoring system 10 in FIG. 1 together with the host system 14. The operations of the monitoring unit 24 are shown on the right side of FIG. 2, while the operations of the host system 14 and its central processing unit 22 are shown on the left side.

The operations shown in FIG. 2 begin with a transmission of a data package A from one monitoring unit 24 to one access point 16, 18, 20 of the host system 14 (step 100). This data package A is sent at one selected point of time and contains the following information:

physiological status data P that have been acquired immediately before the point of time of transmission of the data package A, or that have been collected in a larger time period before a point of time of transmission;

data indicating the remaining battery lifetime L of this monitoring unit 24;

a time stamp, indicating the point of time of the transmission of this data package A; and the expected point of time $T_B$ of the next data transmission, i.e. the transmission of the next data package B.

All data packages A, B, etc. may have the same structure as indicated above.

The data package A is transmitted wirelessly to the access point 16, 18, 20 and forwarded to the central processing unit 22 for further analysis. The central processing unit 22 receives the data package A (step 102) and analyzes it. For example, the physiological status data P referring to the patient who wears the respective monitoring unit 24 from which the data package A originates are analyzed in view of critical status data. Moreover, the expected point of time of the next data transmission $T_B$ is analyzed (step 104).

The host system 14 registrates that no further data packages will be received before the expiration of time $T_B$. With respect to the monitoring unit 24 that has sent the data package A, the host system waits for the expiration of $T_B$. At the time $T_B$, it is checked by the host system 14 whether the following data package B has been received (step 106). When this data package B is sent to an access point 16, 18, 20 at the time $T_B$, the steps 102 and 104 are carried out as described above, that means that the data package B is analyzed with respect to critical physiological status data P and the expected point of time of the next data transmission $T_C$ of another data package C, that is also communicated in form of time related data contained in the data package B. The host system 14 will then wait until the time $T_C$ is expired, will check whether the next data package C has arrived, and so on.

FIG. 2 also describes the case in which the data package B does not arrive at the expected point of time $T_B$ of the transmission of this data package B. In this case the host system 14 will determine that no data package B has been received at time $T_B$ and will output a respective notification to a user (step 108). This notification indicates that no current status data are available from the respective monitoring unit 24, also indicating the identity of the patient 12 who wears the respective monitoring unit 24 and the time expired since the last reception of the status data from this monitoring unit. This time notification may be updated regularly.

After the expiration of $T_B$ at the output of the notification (step 108), the host system 14 will further wait for the next data package B. After another delay time has expired after the time of notification, the host system will output an alarm signal, indicating that no further data has been received from the respective monitoring unit 24. This means that the alarm will not be output immediately when the expected point of time $T_B$ of the transmission of the data package B has expired, but the notification will be output first, and the alarm will be delayed for another time d1 after $T_B$ so that the nursing staff personal is alarmed only when there is a larger time period of no data transmission from the monitoring unit 24. This situation can appear due to an interruption of the connection between the monitoring unit 24 and the host system 14. The patient monitoring system 10 will tolerate an expiration of the expected point of time $T_B$ of the next data transmission, because it is acknowledged that the patient 12 may actually be in a zone 32 (FIG. 1) in which no data transmission is possible. However, if such a time period of no data transmission is extended, the alarm will be output (step 110), indicating a critical status that demands an intervention.

The length of the time delay d1 can be set according to different principles. For example, the time delay d1 may be a fixed time period with a predetermined length. Another possibility is to set the time delay d1 depending on present physiological status data received by the patient. For example, the time delay can be shortened in case the physiological status of the patient has a tendency to deteriorate. Alternatively the time delay d1 depends on time intervals for measuring the physiological status data. For example, when a selected physiological parameter is to be measured within determined measurement periods, the length of the time delay d1 may correspond to one measurement period so that the host system 14 waits for another measurement period before generating an alarm. The time delay d1 can also be calculated based on different measurement periods for different physiological parameters. For example, the delay time d1 for generating the alarm may be based on the shortest of these measurement periods, on the longest of these measurement periods, or be calculated depending on more than one measurement period. One example for a physiological parameter to be measured is the Non Invasive Blood Pressure (NBP), to measured in intervals of 1 hour, while a second physiological parameter could be SpO2 to be measured each 15 minutes. From these measurement periods, one is chosen to be waited for (i.e., the delay time d1 is adapted correspondingly) before generating the alarm, or the time d1 is calculated on the basis of both. However, these examples only represent different embodiments to calculate the delay time d1, and it is possible to calculate d1 on a more complex basis.

It is further understood that during the time period d1, the host system 14 checks whether the next expected data package is received. If this is the case, the host system 14 will go on with analysing the data package that has been received recently and will not generate the alarm.

The host system 14 may handle different monitoring units 24, display the present status of these monitoring units 24 on a display in an order of priority of an intervention, depending on their critical status. For example, patients 12 with monitoring unit 24 has not transmitted data for the longest time period may have the highest ranking in this order. It is also possible to provide an escalation mechanism when generating the alarm. For example, a first alarm in step 110 is output after the time delay d1, while a second alarm with higher intensity may be output after the expiration of an additional time delay d2 so that the intensity of the alarm signals increases with the time expired since the expected point of time $T_B$ of data transmission. The length of the additional time delay d2 may be fixed but can also be calculated on the basis of the present physiological status of the patient or depending on measurement periods of physiological status data to be measured, as described above with relation to the first time delay d1. In the same way, during the time period d2 it is further monitored whether the next expected data package is received, and instead of generating a further alarm, host system 14 will go on with analysing the data package that has been received recently.

It is noted that an alarm signal can also be output when the analysis of the data packages A, B, etc. reveals that the remaining battery lifetime L of the corresponding monitoring unit 24 is low.

It is possible to transmit status data, including the physiological status data P and/or data indicating the priority of an intervention, to an external monitoring system that is connected to the shown host system 14 via a wireless or wirebound connection or interface.

Figure 3:
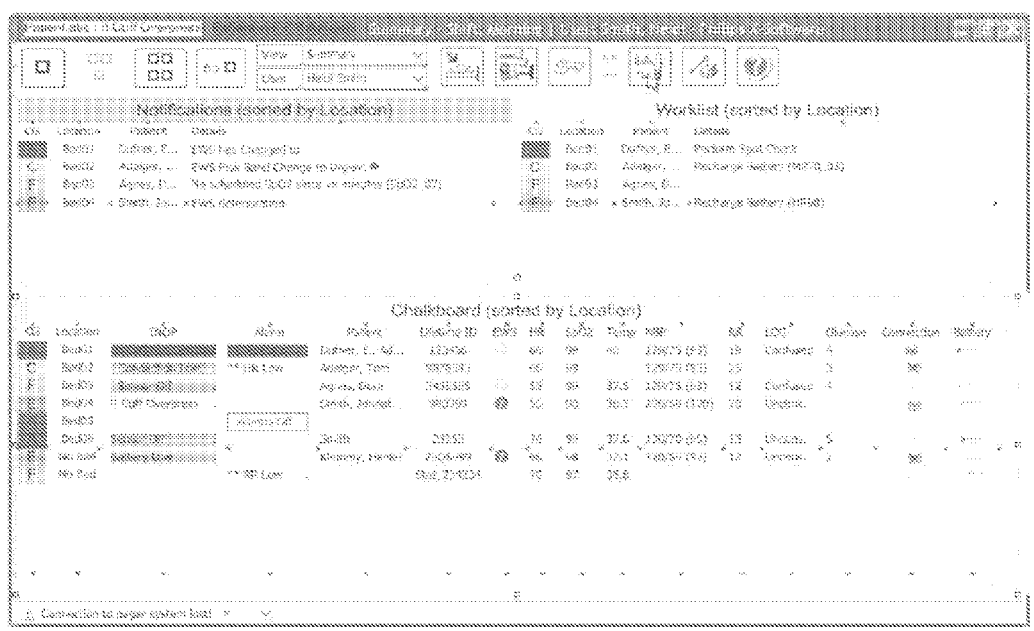
FIG. 3 illustrates a screen shot of a display indicating data of different patients received from monitoring units according to the invention.

In FIG. 3 a display is shown displaying physiological data of different patients. The display is showing a list of notification in the left upper field, wherein the right upper field a worklist is displayed instructing the nursing staff a certain order of patients to be checked or actions to be solved. In the lower field extending over the whole screen an overview is given sorted by location of all patients having such monitoring unit. The display includes the location, the kind of alarms, a possible reason for the alarm, the name of the patient, an ID of the monitoring unit, a plurality of physiological data like, heart rate, temperature, SpO2, blood pressure, etc, technical information of the connection state and the battery status. By use of different colors the attention of the nursing staff could be increased. Thus, life-threatening alarms could be displayed in red, maybe marked by a flashing light, wherein non-critical information could be display in green. Thus, the nursing staff always has an overview of all patients under his/her supervision, which increased the security for the patients and the hospital while providing a higher flexibility to their patients.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A patient monitoring system, comprising:
    at least one monitoring unit for monitoring the physiological status of a patient; and
    a host system comprising a network of access points for wireless reception of physiological status data from the at least one monitoring unit,
    wherein the at least one monitoring unit is provided to transmit data related to the physiological status to at least one of the access points at selected points of time together with time related data containing information about an expected point of time of next data transmission of this monitoring unit,
    wherein the host system is provided to output an alarm signal delayed for a delay time after the expiration of an expected point of time of a data transmission without a reception of further physiological status data from the respective monitoring unit,
    wherein the delay time is a delay time depending on at least one measurement interval of at least one physiological parameter of the patient; or a delay time depending on the present physiological status of the patient.

2. The patient monitoring system according to claim 1, wherein the host system is provided to output alarm signals of an intensity increasing with the time expired after an expected point of time of a data transmission without a reception of further physiological status data from the respective monitoring unit.

3. The patient monitoring system according to claim 1, wherein the at least one monitoring unit is provided for transmitting physiological status data together with the time related data immediately after measurement of these physiological status data.

4. The patient monitoring system according to claim 1, wherein the expected point of time of next data transmission is determined by the respective monitoring unit.

5. The patient monitoring system according to claim 1, wherein each access point is provided to transmit data to the at least one monitoring unit, wherein preferably the host system is provided to determine and to communicate the expected points of time of the next data transmissions to the at least one monitoring unit.

6. The patient monitoring system according to claim 1, wherein the at least one monitoring unit is provided to transmit data indicating the remaining battery life time of this monitoring unit independently and/or together with the physiological status data and time related data.

7. The patient monitoring system according to claim 1, wherein the host system provided to submit status information to an external monitoring system.

8. The patient monitoring system according claim 1, wherein the host system comprises a display for displaying status information of the at least one monitoring unit.

9. A method for monitoring the physiological status of a patient, comprising:
    measuring physiological status data of a patient by means of a monitoring unit, and
    transmitting the measured physiological status data to an access point together with time related data containing information about an expected point of time of next data transmission of this monitoring unit,
    wherein the method further comprises outputting an alarm signal delayed for a delay time after the expiration of an expected point of time of a data transmission without a reception of further physiological status data from the respective monitoring unit wherein the delay time is a delay time depending on at least one measurement interval of at least one physiological parameter of the patient or a delay time depending on the present physiological status of the patient.

10. The method according to claim 9, further comprising the output of alarm signals of an intensity increasing with the time expired after an expected point of time of a data transmission without a reception of further physiological status data from the respective monitoring unit.

* * * * *